(12) United States Patent
Kinouchi

(10) Patent No.: US 10,911,708 B2
(45) Date of Patent: Feb. 2, 2021

(54) ENDOSCOPE AND ENDOSCOPE SYSTEM

(71) Applicant: OLYMPUS CORPORATION, Tokyo (JP)

(72) Inventor: Hideaki Kinouchi, Mitaka (JP)

(73) Assignee: OLYMPUS CORPORATION, Tokyo (JP)

( * ) Notice: Subject to any disclaimer, the term of this patent is extended or adjusted under 35 U.S.C. 154(b) by 149 days.

(21) Appl. No.: 16/203,704

(22) Filed: Nov. 29, 2018

(65) Prior Publication Data

US 2019/0110015 A1    Apr. 11, 2019

Related U.S. Application Data

(63) Continuation of application No. PCT/JP2017/030041, filed on Aug. 23, 2017.

(30) Foreign Application Priority Data

Dec. 15, 2016 (JP) ................. 2016-243253

(51) Int. Cl.
*H04N 5/40* (2006.01)
*H04N 5/232* (2006.01)
(Continued)

(52) U.S. Cl.
CPC .......... *H04N 5/40* (2013.01); *A61B 1/00009* (2013.01); *A61B 1/00016* (2013.01);
(Continued)

(58) Field of Classification Search
CPC ....... H04N 2005/2255; H04N 5/23245; H04N 5/335; H04N 5/343; H04N 5/345;
(Continued)

(56) References Cited

U.S. PATENT DOCUMENTS 4,891,695 A * 1/1990 Uchikubo .............. A61B 1/042
348/581
5,751,341 A * 5/1998 Chaleki .............. A61B 1/00045
348/65
(Continued)

FOREIGN PATENT DOCUMENTS

EP    1607764 A1    12/2005
EP    2030559 A1    3/2009
(Continued)

OTHER PUBLICATIONS

International Search Report dated Oct. 17, 2017 issued in PCT/JP2017/030041.

*Primary Examiner* — Daniel Chang
(74) *Attorney, Agent, or Firm* — Scully, Scott, Murphy & Presser, P.C.

(57) ABSTRACT

An endoscope system includes: an endoscope including an image pickup device provided in an insertion portion, and configured to pick up an image of a subject to output a binary image signal; a multilevel modulation unit configured to output, through a predetermined transmission path, a multilevel signal obtained by performing multilevel modulation on the binary image signal; and a memory configured to store endoscope information on signal transmission; and a processor including a multilevel demodulation unit configured to receive the multilevel signal through the predetermined transmission path, and obtain and output the binary image signal by multilevel demodulation; and a controller configured to read the endoscope information from the memory, and determine a multilevel number in the multilevel modulation by the multilevel modulation unit based on the endoscope information read to control the multilevel modulation unit.

8 Claims, 12 Drawing Sheets

(51) Int. Cl.
*H04N 5/455* (2006.01)
*A61B 1/00* (2006.01)
*A61B 1/045* (2006.01)
*H04N 5/225* (2006.01)
*G02B 23/24* (2006.01)

(52) U.S. Cl.
CPC .......... *A61B 1/00059* (2013.01); *A61B 1/045* (2013.01); *G02B 23/24* (2013.01); *H04N 5/2256* (2013.01); *H04N 5/2257* (2013.01); *H04N 5/232* (2013.01); *H04N 5/455* (2013.01); *H04N 2005/2255* (2013.01)

(58) Field of Classification Search
CPC .............. H04N 5/3765; A61B 1/00009; A61B 1/00045; A61B 1/04; A61B 1/05; A61B 1/00006; A61B 1/00011; A61B 1/0002; A61B 1/0059; A61B 1/0661
USPC .... 600/109, 118, 101, 104, 180; 348/65, 72, 348/581
See application file for complete search history.

(56) References Cited

U.S. PATENT DOCUMENTS

| | | | | |
|---|---|---|---|---|
| 5,871,439 | A * | 2/1999 | Takahashi | A61B 1/00059 348/74 |
| 6,511,422 | B1 * | 1/2003 | Chatenever | A61B 1/0661 600/180 |
| 2002/0140807 | A1 * | 10/2002 | Abe | H04N 19/507 348/65 |
| 2003/0009083 | A1 * | 1/2003 | Takahashi | A61B 1/00059 600/109 |
| 2005/0117028 | A1 * | 6/2005 | Imaizumi | A61B 1/04 348/222.1 |
| 2005/0280509 | A1 | 12/2005 | Tanaka et al. | |
| 2006/0178558 | A1 * | 8/2006 | Obata | A61B 1/0005 600/109 |
| 2007/0049798 | A1 * | 3/2007 | Urasaki | A61B 1/00011 600/118 |
| 2009/0062617 | A1 | 3/2009 | Mizuyoshi | |
| 2010/0217075 | A1 * | 8/2010 | Shigeta | A61B 1/04 600/104 |
| 2012/0197085 | A1 | 8/2012 | Kato et al. | |
| 2013/0050455 | A1 * | 2/2013 | Yagi | H04N 5/343 348/65 |
| 2016/0295141 | A1 * | 10/2016 | Sone | H04N 7/18 |
| 2016/0345814 | A1 * | 12/2016 | Sidar | A61B 1/128 |

FOREIGN PATENT DOCUMENTS

| | | |
|---|---|---|
| EP | 2460459 A1 | 6/2012 |
| JP | 2006-005651 A | 1/2006 |
| JP | 2009-056248 A | 3/2009 |
| JP | 2011-030667 A | 2/2011 |
| WO | WO 2011/013591 A1 | 2/2011 |

* cited by examiner

FIG. 3

ENCODER N=8

| INPUT 2 | INPUT 1 | INPUT 0 | OUTPUT 8 | OUTPUT 7 | OUTPUT 6 | OUTPUT 5 | OUTPUT 4 | OUTPUT 3 | OUTPUT 2 | OUTPUT 1 |
|---|---|---|---|---|---|---|---|---|---|---|
| 0 | 0 | 0 | 0 | 0 | 0 | 0 | 0 | 0 | 0 | 1 |
| 0 | 0 | 1 | 0 | 0 | 0 | 0 | 0 | 0 | 1 | 1 |
| 0 | 1 | 0 | 0 | 0 | 0 | 0 | 0 | 1 | 1 | 1 |
| 0 | 1 | 1 | 0 | 0 | 0 | 0 | 1 | 1 | 1 | 1 |
| 1 | 0 | 0 | 0 | 0 | 0 | 1 | 1 | 1 | 1 | 1 |
| 1 | 0 | 1 | 0 | 0 | 1 | 1 | 1 | 1 | 1 | 1 |
| 1 | 1 | 0 | 0 | 1 | 1 | 1 | 1 | 1 | 1 | 1 |
| 1 | 1 | 1 | 1 | 1 | 1 | 1 | 1 | 1 | 1 | 1 |

FIG. 6

| DECODER N=8 | | | | | | | | | | |
|---|---|---|---|---|---|---|---|---|---|---|
| INPUT 1 | INPUT 2 | INPUT 3 | INPUT 4 | INPUT 5 | INPUT 6 | INPUT 7 | OUTPUT 3 | OUTPUT 2 | OUTPUT 1 | |
| 0 | 0 | 0 | 0 | 0 | 0 | 0 | 0 | 0 | 0 | |
| 1 | 0 | 0 | 0 | 0 | 0 | 0 | 0 | 1 | 0 | |
| 1 | 1 | 0 | 0 | 0 | 0 | 0 | 0 | 0 | 1 | |
| 1 | 1 | 1 | 1 | 1 | 1 | 0 | 1 | 1 | 1 | |
| 1 | 1 | 1 | 1 | 1 | 1 | 0 | 1 | 0 | 0 | |
| 1 | 1 | 1 | 1 | 1 | 0 | 0 | 1 | 1 | 0 | |
| 1 | 1 | 1 | 1 | 1 | 1 | 1 | 1 | 0 | 1 | |

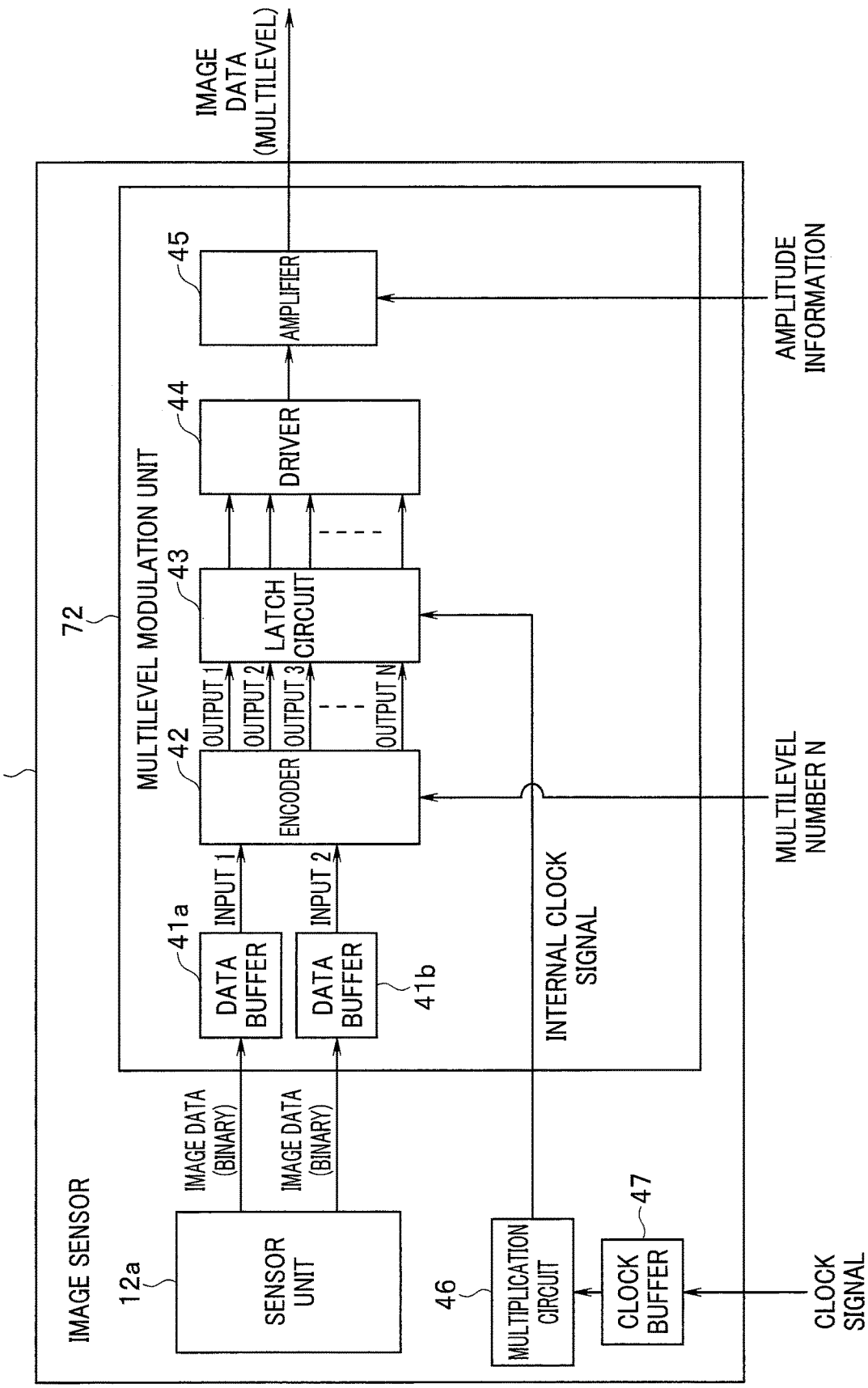

ENDOSCOPE AND ENDOSCOPE SYSTEM

CROSS REFERENCE TO RELATED APPLICATION

This application is a continuation application of PCT/JP2017/030041 filed on Aug. 23, 2017 and claims benefit of Japanese Application No. 2016-243253 filed in Japan on Dec. 15, 2016, the entire contents of which are incorporated herein by this reference.

BACKGROUND OF THE INVENTION

1. Field of the Invention

The present invention relates to an endoscope and an endoscope system which adopt an image pickup device with high resolution.

2. Description of the Related Art

In recent years, endoscopes have been widely used in the medical field for diagnosis, treatment using treatment instruments, and the like. In particular, an electronic endoscope apparatus is commonly used which is provided with an image pickup device such as a CMOS image sensor at the tip of an endoscope insertion portion, and displays an observed image picked up using an image sensor on a television monitor with a video processor.

In recent years, image quality has also been improved in endoscope systems, and not only has the number of pixels of an image pickup device tended to increase, but also a frame rate has tended to increase. Therefore, an amount of transmission of image pickup signals from the image pickup device increases, so it is necessary to extend a transmission bandwidth in a cable that transmits image pickup signals. Although an approach of increasing a signal frequency is conceivable in order to extend the transmission bandwidth, there is a problem that signal processing becomes difficult when the signal frequency is increased, for example. Increasing a diameter of the cable can be a measure to reduce a high-frequency loss. In endoscopes, however, it is necessary to reduce the diameter to facilitate bending and insertion into lumens.

So, a method is conceivable which adopts pulse amplitude modulation (PAM) which is multilevel modulation for image transmission from an endoscope. For example, in Japanese Patent Application Laid-Open Publication No. 2011-30667, an endoscope system is disclosed which uses a multilevel signal to improve a transmission rate without increasing a signal frequency.

In pulse amplitude modulation, a modulated signal obtained by modulating a signal with a PAM modulator (hereinafter referred to as a multilevel signal) has a plurality of amplitudes corresponding to the signal. As the number of the amplitudes of the multilevel signal (hereinafter referred to as a modulation multilevel number or simply a multilevel number) is larger, the number of signal bits which can be transmitted per symbol (baud) of the multilevel signal becomes larger. That is, by increasing the modulation multilevel number, it is possible to improve a transmission rate even at the same symbol rate.

SUMMARY OF THE INVENTION

An endoscope system according to an aspect of the present invention includes: an endoscope including an image pickup device provided in an insertion portion, and configured to pick up an image of a subject to output a binary image signal; a multilevel modulation circuit configured to output, through a predetermined transmission path, a multilevel signal obtained by performing multilevel modulation on the binary image signal; and a memory configured to store endoscope information on signal transmission; and a processor including a multilevel demodulation circuit configured to receive the multilevel signal through the predetermined transmission path, and obtain and output the binary image signal by multilevel demodulation; and a controller configured to read the endoscope information from the memory, and determine a multilevel number in the multilevel modulation by the multilevel modulation circuit based on the endoscope information read to control the multilevel modulation circuit.

An endoscope according to an aspect of the present invention includes: an image pickup device provided in an insertion portion, and configured to pick up an image of a subject to output a binary image signal; a multilevel modulation circuit configured to output a multilevel signal obtained by performing multilevel modulation on the binary image signal; a memory configured to store endoscope information on signal transmission; and a controller configured to determine a multilevel number in the multilevel modulation based on the endoscope information to control the multilevel modulation circuit.

BRIEF DESCRIPTION OF THE DRAWINGS

FIG. 3 is an explanatory diagram showing an example of an encoding table;

FIG. 6 is an explanatory diagram showing a decoding table;

FIG. 12 is a block diagram showing a modification.

DETAILED DESCRIPTION OF THE PREFERRED EMBODIMENT(S)

Embodiments of the present invention will be described below with reference to the drawings.

First Embodiment

Figure 1:
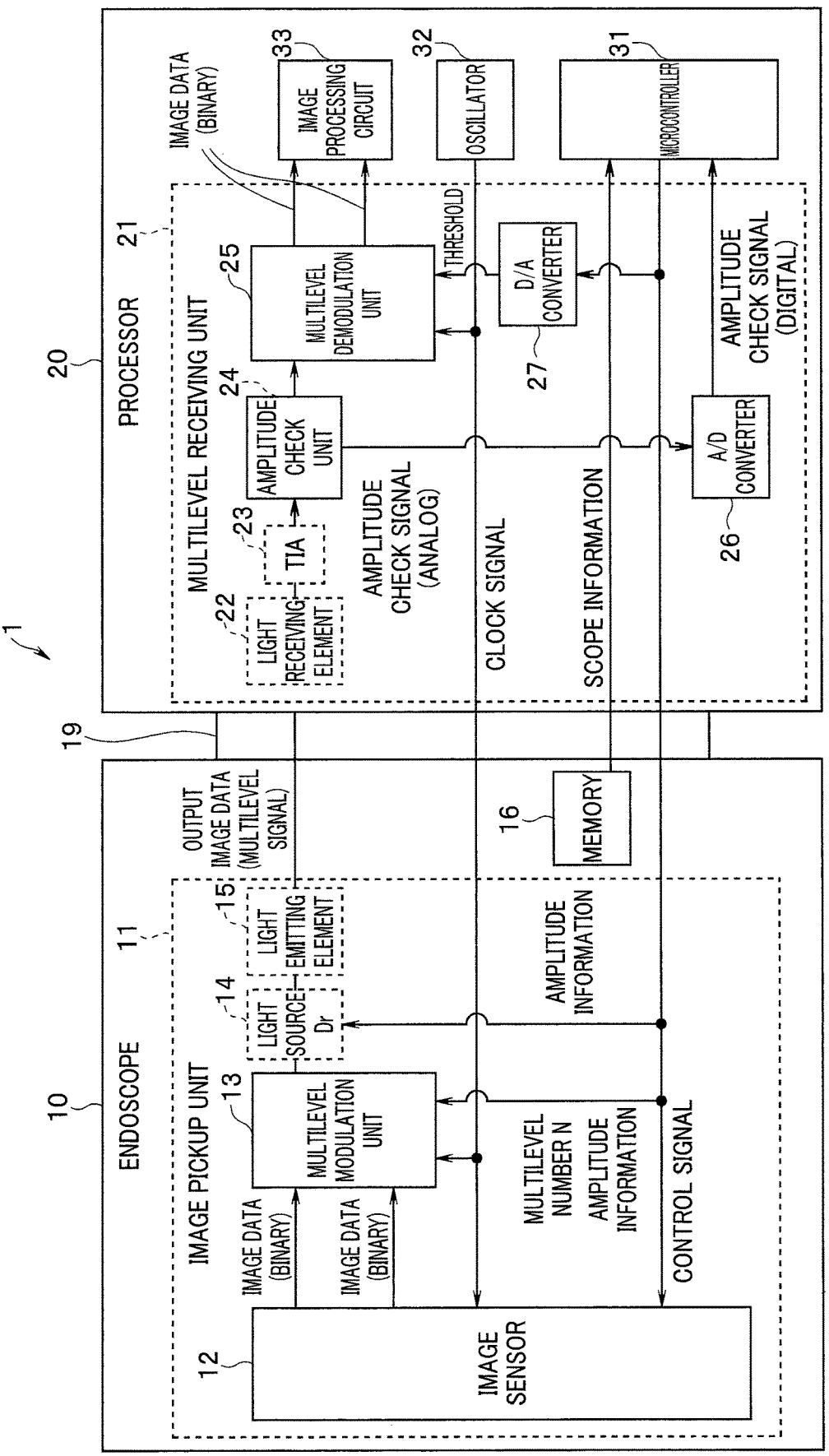
FIG. 1 is a block diagram showing an endoscope system related to a first embodiment of the present invention.

FIG. 1 is a block diagram showing an endoscope system related to a first embodiment of the present invention. The embodiment changes a modulation multilevel number depending on the number of pixels of an image sensor of an endoscope, a frame rate, a scope length, a cable length, a cable diameter, a degree of deterioration, or the like to enable optimal transmission irrespective of a configuration of the endoscope or the like.

An endoscope system 1 is composed of an endoscope 10 and a processor 20. The endoscope 10 has an insertion portion, not shown, which is elongate to be insertable into lumens or the like, and the insertion portion is provided with an image pickup unit 11. The image pickup unit 11 is provided with an image sensor 12 such as a CMOS sensor at a tip of the insertion portion, for example. Note that a CCD may be adopted as the image sensor 12. A cable 19 is extended from a base end side of the insertion portion of the endoscope 10, the endoscope 10 and the processor 20 are removably connected via a connector, not shown, provided at a tip of the cable 19, and signals are transmitted between the image pickup unit 11 and the processor 20.

The endoscope 10 is provided with a memory 16 configured to store various types of information (hereinafter referred to as scope information) including information on the endoscope, for example, information on the number of pixels of the image sensor 12, a frame rate, a scope length, a cable length of the cable 19, and a cable diameter, and information on aged deterioration such as a date of manufacture, that is, information on signal transmission by the endoscope.

Note that the tip of the insertion portion of the endoscope 10 is provided with an illumination window configured to emit illumination light on an object, and light from a light source such as an LED provided inside the endoscope 10 or a light source provided outside the endoscope 10 is transmitted through the insertion portion, so that an object is illuminated from the illumination window as illumination light.

Return light from the object by illumination of the illumination light is incident on an image pickup surface of the image sensor 12. The image sensor 12 is configured to operate according to a clock signal supplied from an oscillator 32 of the processor 20 or a control signal from a microcontroller 31 to photoelectrically convert an incident object optical image to output an image pickup signal based on accumulated electric charges as an image pickup output. Note that the microcontroller 31 can adopt, for example, I2C (inter-integrated circuit) communication to communicate information for controlling the number of reading pixels or a frame rate of the image sensor 12, controlling temperature, etc.

The image sensor 12 is configured to output two lines of binary image data as the image pickup signal. For example, the image sensor 12 may divide one screen into two areas to output image pickup signals in the respective areas as the two lines of image data, or may use an interlace scheme to separate the image pickup output into odd image data and even image data for output in two lines. In addition, for example, the image sensor 12 may separate the image pickup output into two lines of image data in order to reduce an output transmission band. For example, when a transmission band of the image pickup output is 10 Gbps (bits/sec), the image pickup output may be outputted as two lines of image pickup outputs each having a transmission band of 5 Gbps.

Note that as the image sensor 12, one may be adopted which includes a plurality of image sensors, and is configured to output outputs of the respective image sensors as image pickup outputs of respective channels. In addition, the image sensor 12 may be such as to output one line of binary data, or may be such as to output three or more lines of binary data.

The image pickup output of the image sensor 12 is given to a multilevel modulation unit 13. As described later, the multilevel modulation unit 13 performs pulse amplitude modulation on the inputted two lines of image data to output a multilevel signal which is a modulated wave. Note that the multilevel modulation unit 13 may adopt multilevel modulation other than pulse amplitude modulation.

In the embodiment, the multilevel modulation unit 13 is configured to change a modulation multilevel number in multilevel modulation according to the scope information. For example, the multilevel modulation unit 13 is configured to change the multilevel number according to the number of pixels of the image sensor, a frame rate, a scope length, a cable length, a cable diameter, a degree of deterioration, or the like included in the scope information. The multilevel modulation unit 13 outputs the generated multilevel signal as output image data. Note that the multilevel signal from the multilevel modulation unit 13 may be a single end signal or a differential signal.

Figure 2:
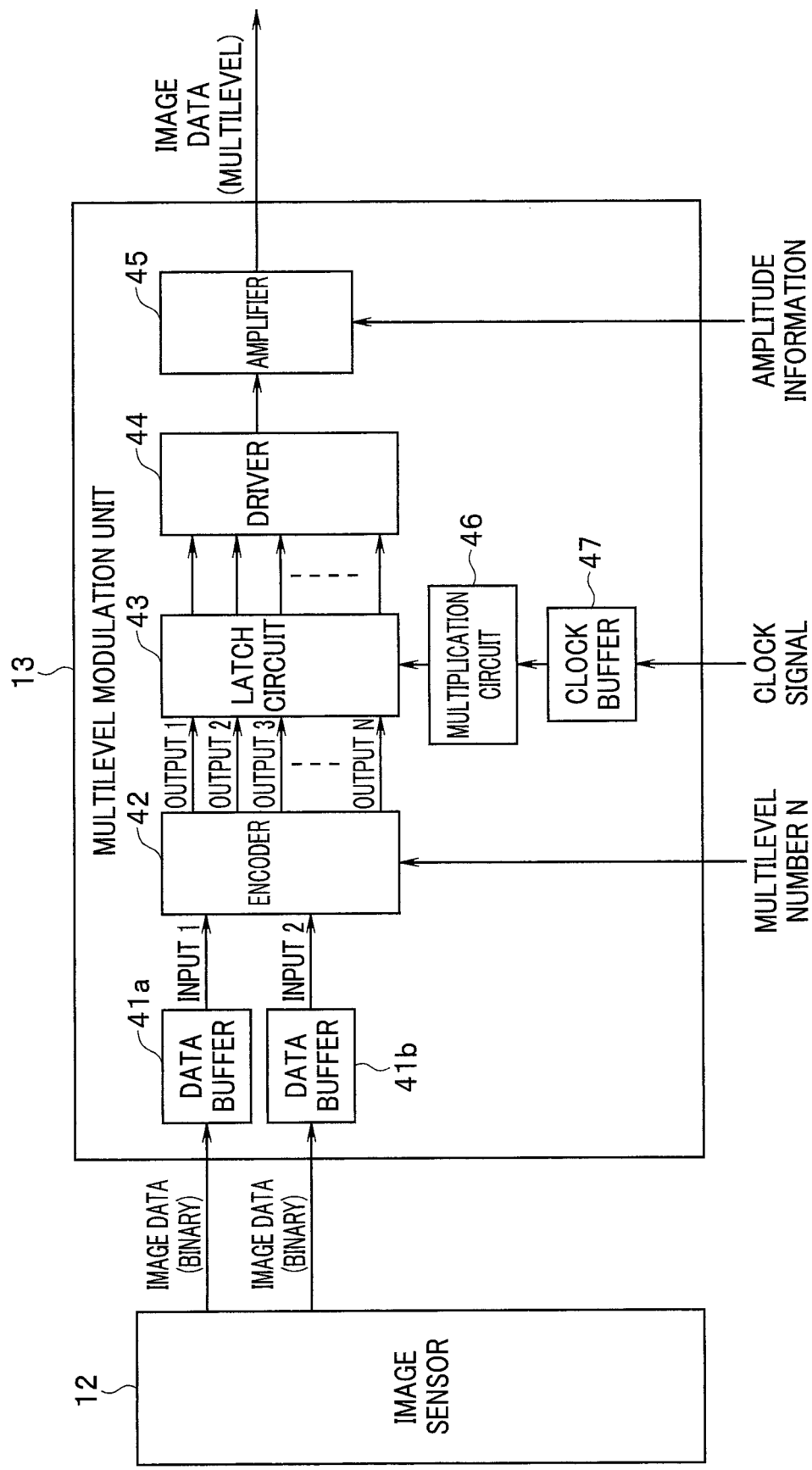
FIG. 2 is a block diagram showing an example of a specific configuration of the multilevel modulation unit 13 in FIG. 1.

FIG. 2 is a block diagram showing an example of a specific configuration of the multilevel modulation unit 13 in FIG. 1. The two lines of image data from the image sensor 12 are given to the encoder 42 through respective data buffers 41a, 41b of the multilevel modulation unit 13. When image data of the number of bits corresponding to the multilevel number has been accumulated, the respective data buffers 41a, 41b simultaneously output the image data to the encoder 42.

For example, in pulse amplitude modulation with a multilevel number of 4 (PAM-4), a multilevel signal has four amplitude levels, and 00, 01, 10 or 11 can be assigned to four amplitude values to transmit data of two bits per symbol. Similarly, in pulse amplitude modulation with a multilevel number of 8 (PAM-8), a multilevel signal has eight amplitude levels, and 000, 001, 010, 011, 100, 101, 110 or 111 can be assigned to eight amplitude values to transmit data of three bits per symbol. That is, in PAM-N with a multilevel number of N, data of $\log_2(N)$ bits per symbol can be transmitted. Consequently, at the same symbol rate, $\log_2(N)$-fold data can be transmitted as compared to binary transmission.

The encoder 42 is supplied with image data for one symbol from the data buffers 41a, 41b simultaneously. The encoder 42 encodes image data for one symbol, that is, $\log_2(N)$ image data in PAM-N into an N-value. For example, the encoder 42 has a memory configured to store an encoding table in which a relationship between an input and an output is written, and is configured to refer to the memory using input image data to output N outputs for setting an amplitude of the N-value.

FIG. 3 is an explanatory diagram showing an example of an encoding table. FIG. 3 shows an example in which the multilevel number N is 8. An example is shown in which an 8-level encoding output is outputted for a 3-bit image input (input 0 to input 2). In FIG. 3, an 8-level encoding output is represented by eight outputs shown in output 1 to output 8. For example, when a 3-bit input shown by input 0, input 1 and input 2 is (000), an encoding output shown by output 1 to output 8 is (10000000). When a 3-bit input shown by input 0, input 1 and input 2 is (110), for example, an encoding output shown by output 1 to output 8 is (11110000). As described later, the eight outputs are used to generate an 8-level multilevel signal.

In addition, FIG. 3 also functions as an encoding table in which the multilevel number N is 4. For a 2-bit image input shown by input 0 to input 1 surrounded by a thick line in FIG. 3, an encoding output shown by output 1 to output 4 is obtained. For example, when a 2-bit input shown by input 0 and input 1 is (10), an encoding output shown by output 1 to output 4 is (1110).

In the embodiment, the encoder 42 is configured so that the multilevel number N is controlled by the microcontroller 31 provided in the processor 20. The microcontroller 31 is configured to operate according to a program stored in a memory, not shown, to read the scope information stored in the memory 16 in the endoscope 10 to determine the multilevel number N based on the scope information. For example, the microcontroller 31 increases the multilevel number N as the number of pixels of the image sensor 12 is larger, and decreases the multilevel number N as the number of pixels of the image sensor 12 is smaller. For example, the microcontroller 31 increases the multilevel number N as the frame rate is higher, and decreases the multilevel number N as the frame rate is lower. For example, the microcontroller 31 decreases the multilevel number N as the scope length or the cable length is longer, and increases the multilevel number N as the length is shorter. For example, the microcontroller 31 increases the multilevel number N as the cable diameter is larger, and decreases the multilevel number N as the cable diameter is smaller. For example, the microcontroller 31 decreases the multilevel number N as a degree of deterioration of the endoscope 10, the cable 19, or the like is larger, and increases the multilevel number N as the degree is smaller.

That is, the microcontroller 31 is configured to set the multilevel number based on a transmission rate of signals transmitted through the cable 19 and a margin between each amplitude value of a multilevel signal and each threshold used for judgment of each amplitude value.

For example, the microcontroller 31 may include a memory, not shown, configured to store a multilevel number table indicating a correspondence between scope information and a multilevel number N, and refer to the multilevel number table stored in the memory based on the scope information to determine the multilevel number N.

In addition, the microcontroller 31 may perform control for changing the number of pixels read from the image sensor 12 or a frame rate. In the case, the microcontroller 31 may be configured to use not only the scope information but also at least one piece of information of information on the number of read pixels and information on the frame rate to determine the multilevel number N. The microcontroller 31 is configured to transmit information on the determined multilevel number N to the multilevel modulation unit 13 in the endoscope 10 through a signal line in the cable 19. The information on the multilevel number N from the microcontroller 31 is supplied to the encoder 42 in the multilevel modulation unit 13.

The encoder 42 performs encoding at the multilevel number N based on the information on the multilevel number N from the microcontroller 31. Note that although the example in FIG. 3 shows an encoding table for encoding in which the multilevel number N is 8 or 4, it is obviously possible to obtain an encoding output corresponding to the predetermined multilevel number of N by preparing an encoding table with a predetermined multilevel number of N. For example, when the multilevel number N is 16, the encoder 42 outputs an encoding output shown by output 1 to output 16 for 4-bit image data.

Each encoding output from the encoder 42 is supplied to a latch circuit 43. The processor 20 is provided with the oscillator 32. The oscillator 32 is configured to generate a clock signal at a predetermined frequency for supply to a clock buffer 47 in the multilevel modulation unit 13 through a clock signal line in the cable 19. The clock buffer 47 outputs the inputted clock signal to a multiplication circuit 46. The multiplication circuit 46 multiplies the inputted clock signal for output to the latch circuit 43.

N encoding outputs from the encoder 42 may have a shift among output timings, and the latch circuit 43 operates according to the clock signal from the multiplication circuit 46 to synchronize N decoding outputs for supply to a driver 44. The driver 44 can be composed of, for example, an adder, and adds N latch outputs to obtain an addition result of voltage values or current values. The addition result of the driver 44 is a multilevel signal at any level of N amplitude levels. That is, the driver 44 consequently outputs an addition result of voltage or current values corresponding to $\log_2(N)$ image data inputted to the encoder 42. The addition result from the driver 44 is supplied to an amplifier 45.

The amplifier 45 is supplied with amplitude information described later for setting each amplitude of a multilevel signal from the microcontroller 31. The amplifier 45 has an amplification factor determined based on the amplitude information, and amplifies the addition result from the driver 44 at the determined amplification factor so that a maximum amplitude to be set of the multilevel signal can be obtained. Consequently, the maximum amplitude of the addition result from the driver 44 is amplified up to a predetermined amplitude level, and multilevel image data with a voltage or current value corresponding to input image data is outputted from the amplifier 45.

Note that although an example is described in FIG. 2 in which the amplifier 45 is given the amplitude information to control an amplitude of a multilevel signal, the encoder 42 may be given the amplitude information to be controlled to output an encoding output considering the amplitude of the multilevel signal.

As seen above, in the embodiment, the multilevel modulation unit 13 generates a multilevel signal with the multilevel number N based on the scope information for output as output image data.

The output image data from the multilevel modulation unit 13 is supplied to a light source driver (light source Dr) 14. The light source driver 14, a light emitting element 15, a light receiving element 22 and a transimpedance amplifier (hereinafter, referred to as a TIA) 23 surrounded by dashed lines in FIG. 1 show circuit components necessary for optical transmission processing for the output image data from the multilevel modulation unit 13. In optical transmission, a cable into which an optical fiber is inserted is adopted as the cable 19. Note that when optical transmission processing for the output image data from the multilevel modulation unit 13 is not performed but an electric signal is transmitted as it is, a cable into which a metal wire is inserted is adopted as the cable 19, and the circuit components are omitted.

The light source driver 14 is given multilevel output image data to give a driving signal corresponding to the output image data to the light emitting element 15 to drive the light emitting element 15. As the light emitting element 15, a semiconductor laser such as a surface emitting laser (VCSEL) can be adopted. The light emitting element 15 is configured to emit light at an amplitude level based on the driving signal from the light source driver 14.

Thus, the light emitting element 15 has an amplitude level of light output controlled by the light source driver 14 to transmit output image data which is an optical multilevel signal. The output image data from the light emitting element 15 is given to the light receiving element 22 composing a multilevel receiving unit 21 in the processor 20 through the optical fiber inserted into the cable 19. Note that when the output image data from the multilevel modulation unit 13 is transmitted as an electric signal as it is, the output image data from the multilevel modulation unit 13 is given to an amplitude check unit 24 and a multilevel demodulation unit 25 composing the multilevel receiving unit 21 in the processor 20 through the metal wire inserted into the cable 19.

As the light receiving element 22, a photodiode can be adopted. The light receiving element 22 receives the optical multilevel signal transmitted through the optical fiber for giving to the TIA 23. The TIA 23 is configured to output a voltage value or a current value with an amplitude corresponding to the optical multilevel signal. For example, the TIA 23 is configured to detect current flowing through the light receiving element 22 and amplify a detected current value for conversion into a voltage and output. Note that the TIA 23 may be configured to be able to amplify the current value detected from the light receiving element 22 for output as it is. The output of the TIA 23 is given to the amplitude check unit 24 and the multilevel demodulation unit 25.

The amplitude check unit 24 checks an amplitude level of the inputted multilevel signal. When the multilevel signal from the endoscope 10 is transmitted through the metal wire, the amplitude check unit 24 may perform amplitude check based on the voltage or current value of the received multilevel signal. In addition, when the multilevel signal from the endoscope 10 is transmitted through the optical fiber, the amplitude check unit 24 may perform amplitude check based on the voltage value of the multilevel signal from the TIA 23, and may also perform amplitude check based on the current value of the multilevel signal from the TIA 23. The amplitude check unit 24 may use an eye pattern of the multilevel signal to perform amplitude check to calculate each amplitude level.

In order to demodulate the multilevel signal, it is necessary to accurately grasp a level of each amplitude of the multilevel signal. Since the multilevel signal may change in level depending on transmission property, the amplitude check unit 24 is configured to check the amplitude of the multilevel signal from the received signal to accurately calculate the amplitude level of the transmitted multilevel signal. The amplitude check unit 24 outputs a signal (hereinafter, referred to as an amplitude check signal) of an amplitude level of the multilevel signal. The A/D converter 26 outputs to the microcontroller 31 amplitude check information obtained by converting the amplitude check signal from the amplitude check unit 24 into a digital signal.

The microcontroller 31 generates the amplitude information for controlling the amplitude of the multilevel signal based on the amplitude check information to control the multilevel modulation unit 13 and the light source driver 14. For example, the microcontroller 31 may include a memory, not shown, configured to store an amplitude control table indicating a correspondence between the amplitude check information and the amplitude information, and be configured to refer to the amplitude control table stored in the memory based on the amplitude check information to calculate the amplitude information.

The microcontroller 31 is also configured to determine a threshold to be used for amplitude judgment in demodulation as described later based on the amplitude check information. For example, the microcontroller 31 may include a memory, not shown, configured to store a demodulation threshold table indicating a correspondence between the amplitude check information and a threshold in demodulation, and refer to the demodulation threshold table stored in the memory based on the amplitude check information to calculate the threshold in demodulation. The D/A converter 27 is configured to convert the threshold in demodulation from the microcontroller 31 into an analog signal for supply to the multilevel demodulation unit 25 as a threshold.

The multilevel demodulation unit 25 is configured to be supplied with the threshold to be used in demodulation from the D/A converter 27, and use the threshold to demodulate the inputted multilevel signal. The multilevel demodulation unit 25 outputs two lines of original binary data before modulation obtained by demodulation to an image processing circuit 33. In the embodiment, the multilevel demodulation unit 25 is configured to be given information on the multilevel number from the microcontroller 31, and perform multilevel demodulation processing corresponding to a modulated signal to obtain original image data before modulation.

Figure 4:
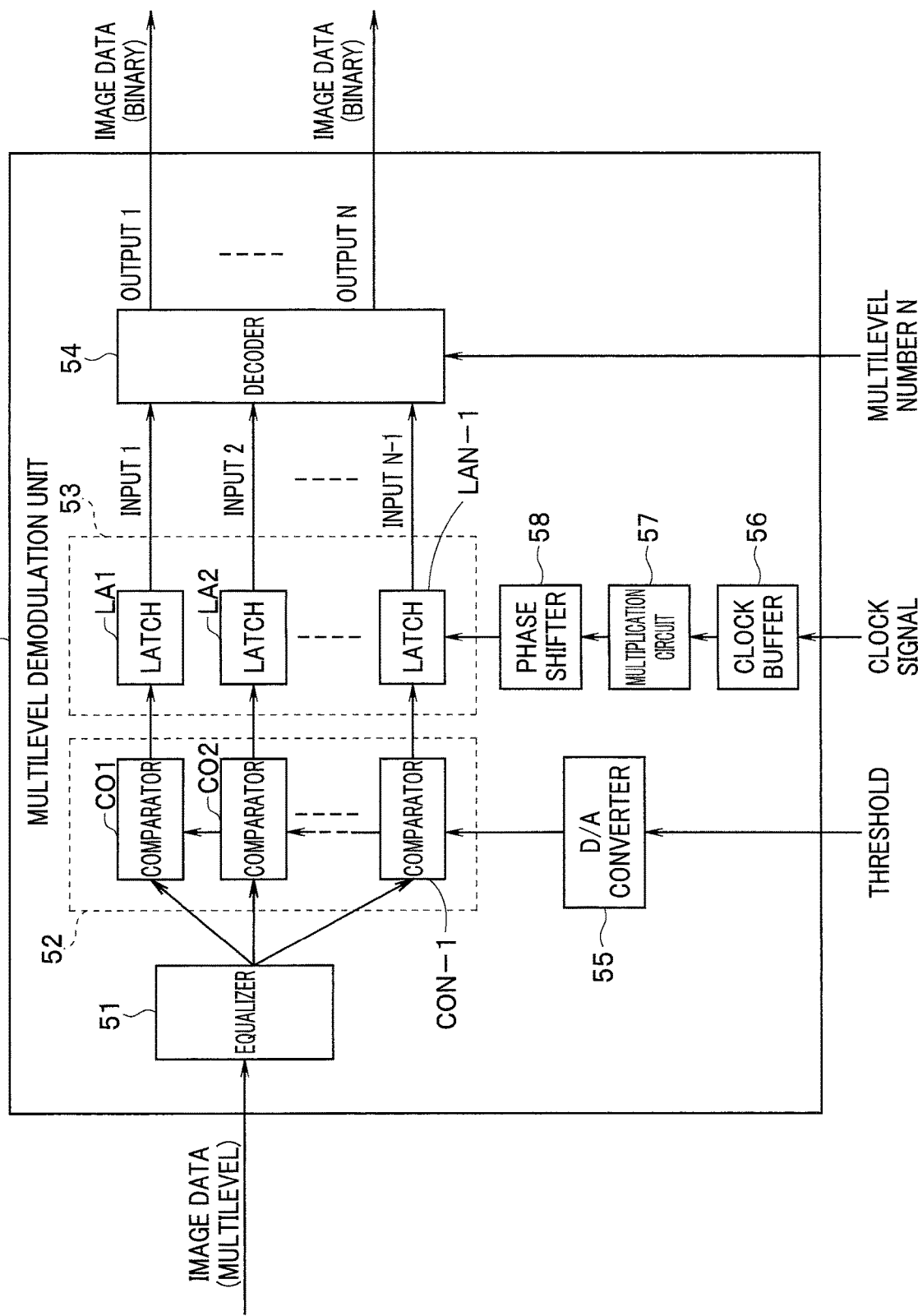
FIG. 4 is a block diagram showing an example of a specific configuration of the multilevel demodulation unit 25 in FIG. 1.

FIG. 4 is a block diagram showing an example of a specific configuration of the multilevel demodulation unit 25 in FIG. 1. The multilevel signal inputted to the multilevel demodulation unit 25 is given to an equalizer 51. The equalizer 51 performs waveform shaping of the inputted multilevel signal. Consequently, threshold judgment for binarization becomes easy. An output of the equalizer 51 is given to respective comparators CO1, CO2, . . . , CON-1 (hereinafter, respective comparators are collectively referred to as comparators CO) of a comparator circuit 52.

The comparator circuit 52 has (N-1) comparators CO with respect to the multilevel number N, and the output of the equalizer 51 is given to one input end of each of the comparators CO. The other input end of each comparator CO is given a threshold generated for each comparator CO by the microcontroller 31. The microcontroller 31 generates each threshold to be supplied to each comparator CO based on the amplitude check information of the amplitude check unit 24. The microcontroller 31 judges N respective amplitudes of the multilevel signal at the multilevel number N based on the amplitude check information, and sets each threshold to an intermediate value between amplitudes with adjacent amplitude values. Accordingly, the microcontroller 31 consequently sets (N-1) thresholds for the multilevel signal with the multilevel number N.

The N-1 thresholds from the microcontroller 31 are given to a D/A converter 55 in the multilevel demodulation unit 25. The D/A converter 55 converts digital thresholds into analog ones, and gives the (N-1) analog thresholds to the other input ends of the comparators CO, respectively. Thus, each of the comparators CO1 to CON-1 compares the inputted threshold with the output of the equalizer 51 to output a comparison result to a latch circuit 53.

Figure 5:
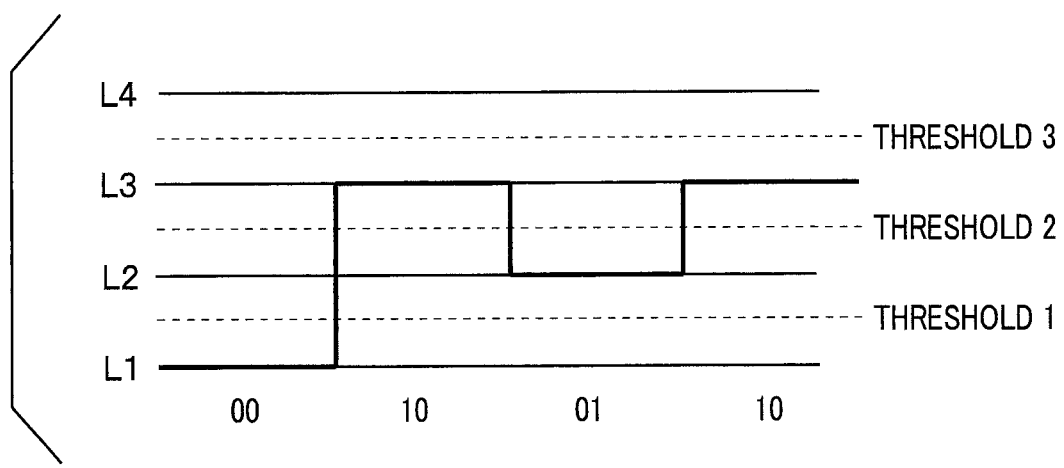
FIG. 5 is an explanatory diagram for explaining thresholds.

FIG. 5 is an explanatory diagram for explaining thresholds, and is for explaining settings in a case where the multilevel number corresponding to the encoding table in FIG. 3 is 4. The microcontroller 31 sets respective intermediate values of four amplitude values L1-L4 as three thresholds 1-3 corresponding to a multilevel number of 4. The thresholds 1-3 are converted into analog values, and given to the other input ends of the comparators CO1-CO3, respectively. In the case, the comparators CO1-CO3 make a comparison of the threshold 1 with the output of the equalizer 51, a comparison of the threshold 2 with the output of the equalizer 51, and a comparison of the threshold 3 with the output of the equalizer 51, respectively, to output comparison results. For example, the comparators CO1-CO3 output a high level (hereinafter, referred to as an H level) when the level of the multilevel signal from the equalizer 51 is higher than the levels of the thresholds 1-3, and output a low level (hereinafter, referred to as an L level) when the level of the multilevel signal is lower than the levels of the thresholds 1-3.

For example, when the level of the inputted multilevel signal is L1 in FIG. 5, outputs of the comparators CO1-CO3 are L, L, and L levels, respectively. When the level of the multilevel signal is L2, outputs of the comparators CO1-CO3 are H, L, and L levels, respectively. Similarly, when the level of the multilevel signal is L3, outputs of the comparators CO1-CO3 are H, H, and L levels, respectively, and when the level of the multilevel signal is L4, outputs of the comparators CO1-CO3 are H, H, and H levels, respectively. That is, based on outputs of the (N-1) comparators CO, it is known which of N amplitudes the multilevel signal has.

For example, it is assumed that amplitude levels of results obtained by converting 2-bit image data (00)(10)(01)(10) into multilevel signals in modulation according to the encoding table in FIG. 3 can be represented by L1, L3, L2, and L3 as shown by a thick line in FIG. 5. In the case, from the comparators CO1-CO3, (LLL)(HHL)(HLL)(HHL) are consequently outputted.

Outputs of respective comparators CO of the comparator circuit 52 are supplied to respective latches LA1, LA2, . . . , LAN-1 (hereinafter, respective latches are collectively referred to as latches LA) composing the latch circuit 53. Considering a case where a shift occurs due to wiring delay or the like, the respective latches LA match timings of outputs of the comparators CO with each other for giving to the decoder 54. That is, a clock from the oscillator 32 is given to a multiplication circuit 57 via a clock buffer 56. The multiplication circuit 57 multiplies the clock for giving to a phase shifter 58. The phase shifter 58 matches the multiplied clock with a predetermined phase for supply to all the latches LA. Consequently, the latches LA simultaneously give outputs of all the comparators CO to the decoder 54 at a clock timing from the phase shifter 58.

The decoder 54 performs decoding processing corresponding to encoding processing in the multilevel modulation unit 13 to return the multilevel signal to a binary signal. The decoder 54 may use a decoding table corresponding to the encoding table used by the multilevel modulation unit 13 for binarization.

FIG. 6 is an explanatory diagram showing an example of a decoding table, and corresponds to the encoding table in FIG. 3. That is, FIG. 6 shows an example in which the multilevel number N is 8. An example is shown in which for comparator outputs (input 1 to input 7) with respect to an 8-level multilevel signal, 3-bit image data (output 1 to output 3) is outputted as a decoding output.

FIG. 6 also functions as an encoding table in which the multilevel number N is 4. For three comparator outputs indicated by input 1 to input 3 surrounded by a thick line in FIG. 6, 2-bit image data indicated by output 1 to output 2 is obtained as a decoding output.

For example, it is assumed that a multilevel signal with a lowest amplitude value level of L1 (see FIG. 5) is obtained from the driver 44 for an encoding output (1000) in FIG. 3 with 2-bit image data before encoding corresponding to (00). Similarly, it is assumed that a multilevel signal with an amplitude value level of L2 is obtained from the driver 44 for an encoding output (1100) with respect to 2-bit image data (01) before encoding. It is also assumed that a multilevel signal with an amplitude value level of L3 is obtained from the driver 44 for an encoding output (1110) with respect to 2-bit image data (10) before encoding, and a multilevel signal with an amplitude value level of L4 is obtained from the driver 44 for an encoding output (1111) with respect to 2-bit image data (11) before encoding.

For the level L1 of a multilevel signal corresponding to 2-bit image data (00) before multilevel modulation, outputs of the comparators CO1-CO3 are L, L, and L levels, respectively, as described above, that is, a logical value of (000). That is, in the case, input 1 to input 3 in FIG. 6 are (000), and a 2-bit decoding output (output 1, output 2) is the same image data (00) as before multilevel modulation. Similarly, for the level L2 of a multilevel signal corresponding to 2-bit image data (01) before multilevel modulation, outputs of the comparators CO1-CO3 are H, L, and L levels, respectively, that is, a logical value of (100). In the case, input 1 to input 3 in FIG. 6 are (100), and output 1 and output 2 are the same image data (01) as before multilevel modulation. Similarly, for the level L3 of a multilevel signal corresponding to 2-bit image data (10) before multilevel modulation, outputs of the comparators CO1-CO3 are a logical value of (110), and a corresponding decoding output from FIG. 6 is the same image data (10) as before multilevel modulation. Similarly, for the level L4 of a multilevel signal corresponding to 2-bit image data (11) before multilevel modulation, outputs of the comparators CO1-CO3 are a logical value of (111), and a corresponding decoding output from FIG. 6 is the same image data (11) as before multilevel modulation. When the multilevel number is 8, the decoder 54 can also use the decoding table in FIG. 6 for decoding to acquire image data before encoding.

Note that although FIG. 6 shows an example with a multilevel number of 8 or 4, it is obviously possible to obtain a decoding output corresponding to the predetermined multilevel number of N by preparing a decoding table at a predetermined multilevel number of N.

An output of the decoder 54 is given to the image processing circuit 33 as an output of the multilevel demodulation unit 25 composing the multilevel receiving unit 21. In the case, the multilevel demodulation unit 25 outputs a decoding result of the decoder 54 as two lines of binary image data similarly to an output from the image sensor 12. The image processing circuit 33 performs predetermined image signal processing on the inputted image data. For example, the image processing circuit 33 performs various types of image signal processing such as gamma correction processing, dimming processing, white balance adjustment processing, and matrix processing. An image signal obtained through image processing by the image processing circuit 33 is supplied to a monitor or a recording apparatus, not shown, to be used for display or recording.

Next, operation of the thus-configured embodiment will be described.

The endoscope 10 and the processor 20 are connected via the cable 19 extended from the base end side of the endoscope 10. The microcontroller 31 of the processor 20 reads the scope information from the memory 16 provided in the endoscope 10 through a wire in the cable 19.

The scope information includes the number of pixels of the image sensor 12, a frame rate, a scope length, a cable diameter of the cable 19, and a cable length, which are information on signal transmission of the endoscope 10, and information on aged deterioration such as a date of manufacture. The microcontroller 31 determines the multilevel number N in multilevel modulation used for image transmission based on the scope information.

Information on the multilevel number N from the microcontroller 31 is supplied to the multilevel modulation unit 13 in the endoscope 10. The image sensor 12 is controlled by the microcontroller 31 to pick up an image of an object to obtain a picked-up image. Binary image data is outputted from the image sensor 12.

The binary image data from the image sensor 12 is given to the multilevel modulation unit 13. The multilevel modulation unit 13 performs pulse amplitude modulation on the inputted binary image data at the multilevel number N set by the microcontroller 31 to generate a multilevel signal. The multilevel signal has a multilevel number of N, and when the baud rate is the same, it is possible to perform data transmission of $\log_2(N)$-fold amount of data as compared to in transmitting binary image data.

Consequently, for example, even when the cable diameter of the cable 19 is made relatively small, it is possible to reduce a transmission loss by making a signal frequency in transmission relatively low, so that stable signal transmission is possible. In addition, for example, even when the resolution of an image to be transmitted is high, stable signal transmission is possible without increasing the cable diameter.

The multilevel number N is set based on the scope information. For example, in a case where the cable diameter is relatively large, the multilevel number N is set to a relatively small value. Accordingly, in the case, the multilevel signal can have a relatively large difference between adjacent amplitude levels, a margin is generated in a difference between each amplitude value and each threshold, it is possible to reliably judge an amplitude even when noise or the like is mixed, and reliability of demodulation is improved to enable stable signal transmission.

The multilevel signal from the multilevel modulation unit 13 is given to the light source driver 14 in the case of optical transmission, and is supplied to the processor 20 through the cable 19 in the case of transmission using an electric signal through a metal wire.

In the case of optical transmission, the light source driver 14 drives the light emitting element 15 based on the multilevel signal to supply an optical multilevel signal to the processor 20 though the optical fiber in the cable 19. The light receiving element of the processor 20 receives the optical multilevel signal, and the TIA 23 gives a multilevel signal of a current value or a voltage value based on the received optical multilevel signal to the amplitude check unit 24 and the multilevel demodulation unit 25.

The amplitude check unit 24 checks the amplitude of the multilevel signal to output an amplitude check signal. The amplitude check signal is converted by the A/D converter 26 into a digital signal, and supplied to the microcontroller 31. The microcontroller 31 calculates thresholds to be used in the multilevel demodulation unit 25 based on the amplitude check signal, and generates amplitude information for controlling the amplitude of the multilevel signal in modulation. The amplitude information from the microcontroller 31 is supplied to the image pickup unit 11 to be used for amplitude control of the multilevel signal.

Information on thresholds from the microcontroller 31 is converted by the D/A converter 27 into analog signals, and is then supplied to the multilevel demodulation unit 25. The multilevel demodulation unit 25 uses the thresholds to demodulate the inputted multilevel signal to obtain original binary image data.

Since the multilevel number N is determined based on the scope information, a multilevel number higher than necessary is not set. And the thresholds are set to a value corresponding to the multilevel number N. Therefore, depending on the configuration of the endoscope, it is possible to set a difference between an amplitude of the multilevel signal and a threshold to a sufficiently large value, so that reliable multilevel demodulation is possible.

Binary image data before modulation is recovered by the multilevel demodulation unit 25. The binary image data from the multilevel demodulation unit 25 is outputted to the image processing circuit 33 at the same number of output lines as the number of output lines from the image sensor 12. The image processing circuit 33 performs predetermined signal processing on the inputted image data for output to a monitor or a recording apparatus, not shown.

As seen above, in the embodiment, by using multilevel amplitude modulation, it is possible to improve a transmission rate even at the same symbol rate. Accordingly, even an image signal with a relatively high resolution at a relatively high frame rate acquired by the endoscope can be transmitted to post-stage circuits at a relatively low signal frequency. Consequently, not only signal processing in post-stage circuits becomes easy, but also a loss due to a cable for transmitting a signal is reduced, so that the cable can be made sufficiently thin to enable reduction of the diameter of the endoscope. Then, the embodiment is configured so that the multilevel number in multilevel amplitude modulation can be changed based on the scope information. Consequently, it is possible to perform multilevel amplitude modulation at an optimum multilevel number corresponding to the type or the like of the endoscope, the cable, or the like. Accordingly, it is possible to prevent a case where the multilevel number is increased more than necessary, which makes processing in a demodulation circuit difficult causing unstable transmission. For example, when the cable length of the endoscope connected to the processor is short, the multilevel number is made small to facilitate demodulation processing, and conversely, when the cable length is long, the multilevel number is made large to lower a signal frequency, so that transmission with a reduced loss is made possible. As seen above, in the embodiment, by changing the multilevel number based on the scope information, it is possible to stabilize transmission and demodulation processing.

Note that when a minimum amplitude level in the case of equalizing level differences between respective amplitudes of the multilevel signal is assumed to be, for example, 100 mVpp, a maximum amplitude in PAM-2 is 100 mVpp, a maximum amplitude in PAM-4 is 300 mVpp, a maximum amplitude in PAM-8 is 700 mVpp, and a maximum amplitude in PAM-16 is 1500 mVpp. Since increase in a maximum amplitude causes a problem of heat generation, an upper limit of the multilevel number N is practically set to about 16.

Although an example is described in the above embodiment in which the multilevel number is decreased as much as possible within a range in which signal transmission is more stably performed, a multilevel number within a range in which stable signal transmission is ensured also has an advantage of further reducing the diameter of the cable by changing the multilevel number according to the number of output lines from the image sensor.

Figure 7A:
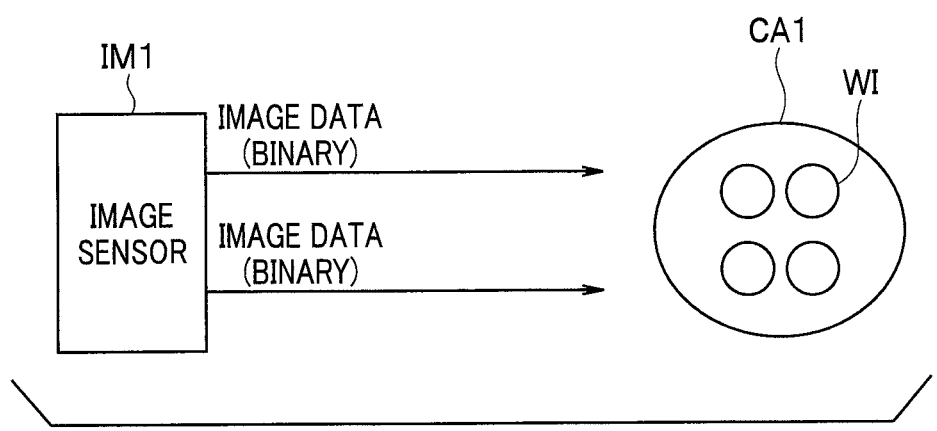
FIG. 7A is an explanatory diagram for explaining an advantage of the embodiment.

FIGS. 7A-10B are explanatory diagrams for explaining the advantage. FIGS. 7A and 8A show examples in which binary image data is transmitted as it is. FIG. 7A shows that an image sensor IM1 outputs two lines of binary image data. When the two lines of image data are transmitted using a differential signal, it is necessary to wire two pairs of, that is, four signal lines WI in a cable CA1 connecting the endoscope and the processor.

For example, in a case where transmission of all image data of the image sensor requires image transmission at 10 Gbps, when a transmission rate enabling stable signal transmission on a pair of signal lines is 5 Gpbs, the transmission may be performed using two lines of signal lines. FIG. 7A is a transmission method which is also adopted in such a case.

Figure 8A:
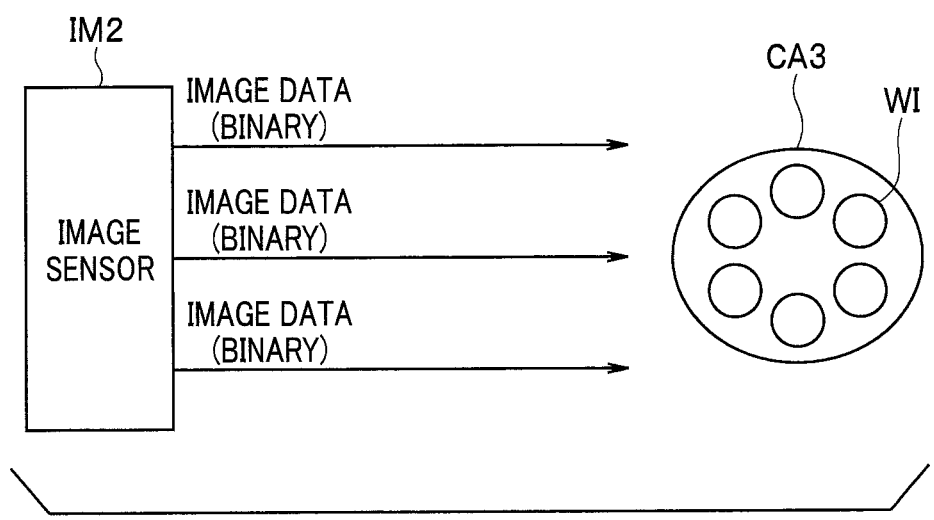
FIG. 8A is an explanatory diagram for explaining an advantage of the embodiment.

In addition, FIG. 8A shows that the image sensor IM1 outputs three lines of binary image data. When the three lines of image data are transmitted using a differential signal, it is necessary to wire three pairs of, that is, six signal lines WI in a cable CA3 connecting the endoscope and the processor.

The approaches in FIGS. 7A and 8A need to wire relatively many signal lines in the cable, and have a problem in terms of reducing the diameter. In order to reduce the diameter, a method using a time division multiplexing scheme is conceivable. By performing time division multiplexing on the two lines of image data from the image sensor, transmission is performed with a pair of signal lines. However, the scheme needs to double a transmission speed, and has a problem in terms of power consumption and a transmission loss.

Figure 7B:
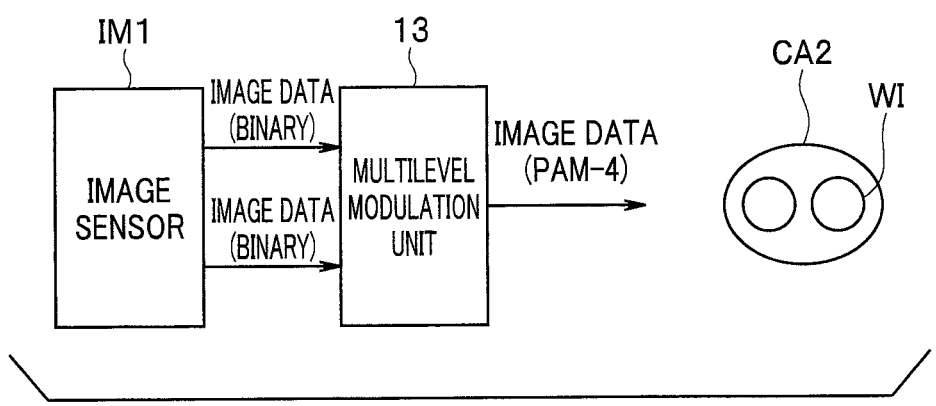
FIG. 7B is an explanatory diagram for explaining an advantage of the embodiment.

In contrast, in the above first embodiment, the microcontroller 31 sets the multilevel number N to 4 based on the scope information when outputting two lines of binary image data. That is, in the case, as shown in FIG. 7B, transmission with a pair of signal lines is possible at the same baud rate as in FIG. 7A. That is, since the multilevel modulation unit 13 can transmit 2-bit image data with one symbol in the configuration in FIG. 7B, a cable CA2 in which a pair of, that is, two signal lines WI are wired should be adopted as a cable connecting the endoscope and the processor in transmission using a differential signal.

Figure 8B:
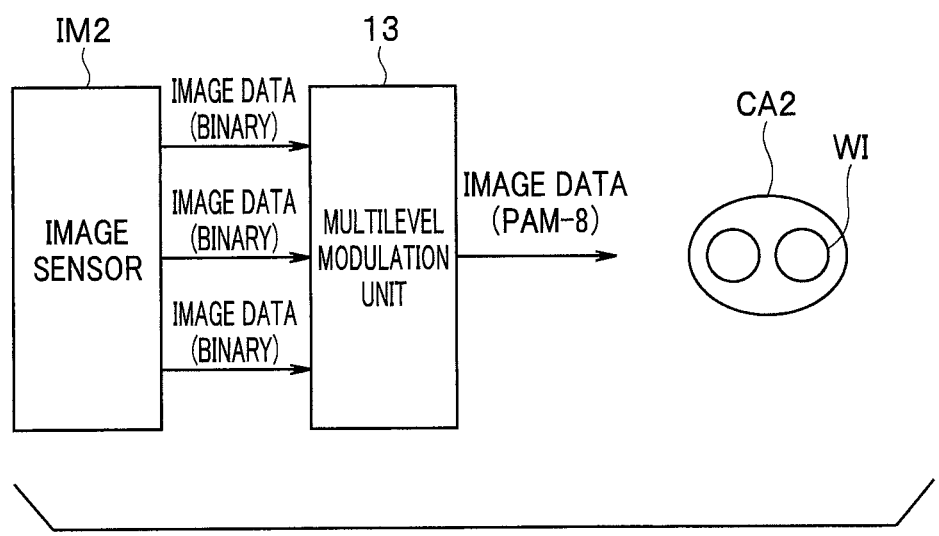
FIG. 8B is an explanatory diagram for explaining an advantage of the embodiment.

Furthermore, when three lines of binary image data are outputted as in FIG. 8A, the microcontroller 31 sets the multilevel number N to 8 based on the scope information. That is, in the case, as shown in FIG. 8B, threefold image data can be transmitted at the same baud rate as in FIG. 8A, and transmission using the cable CA2 in which a pair of (two) signal lines WI are wired is possible. As seen above, by adopting the embodiment, the diameter can be reduced.

Figure 9A:
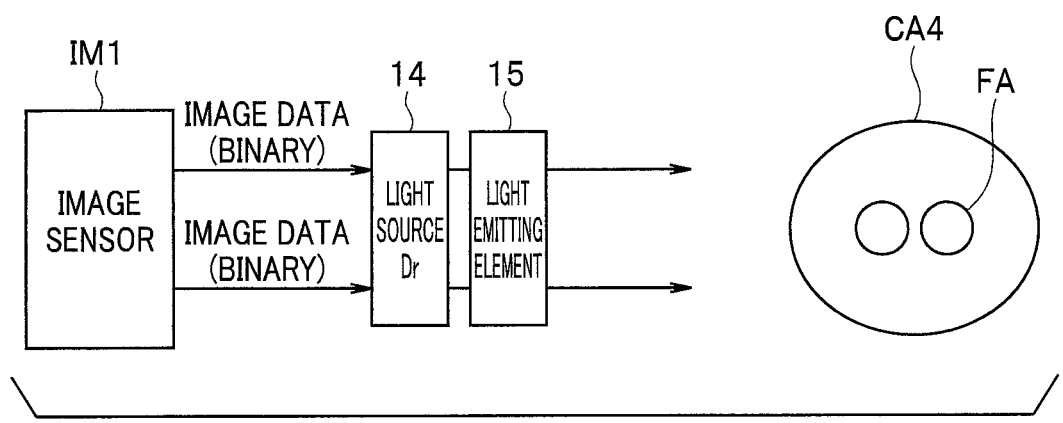
FIG. 9A is an explanatory diagram for explaining an advantage of the embodiment.
Figure 10A:
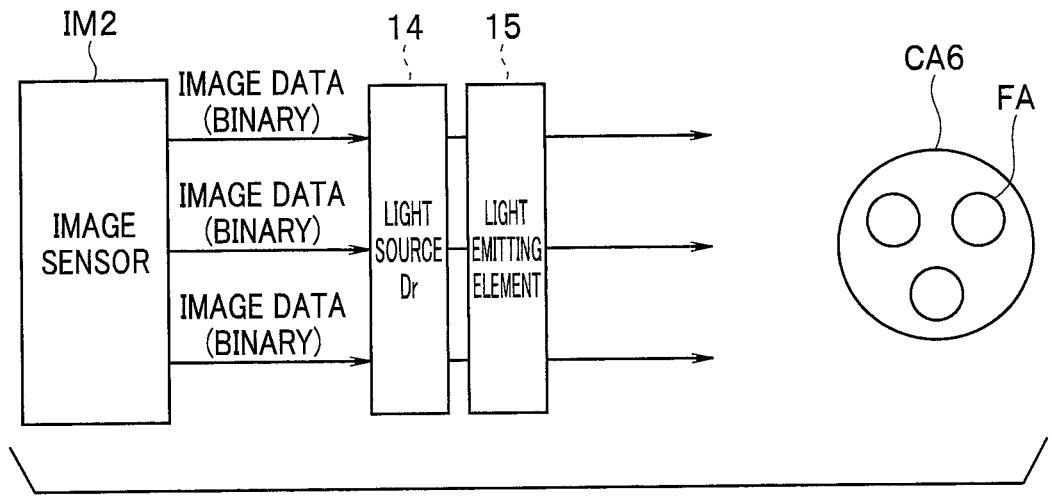
FIG. 10A is an explanatory diagram for explaining an advantage of the embodiment.

FIGS. 9A and 10A show examples in which binary image data is optically transmitted as it is. FIG. 9A shows that the image sensor IM1 outputs two lines of binary image data. When the two lines of image data are optically transmitted using a differential signal, it is necessary to wire two optical fibers FA in a cable CA4 connecting the endoscope and the processor. In addition, FIG. 10A shows that the image sensor IM2 outputs three lines of binary image data. When the three lines of image data are optically transmitted using a differential signal, it is necessary to wire three optical fibers FA in a cable CA6 connecting the endoscope and the processor.

As seen above, the approaches in FIGS. 9A and 10A need to wire relatively many optical fibers in the cable, and have a problem in terms of reducing the diameter. A method using a wavelength multiplexing scheme is conceivable for the problem. Two lines of image data from the image sensor are converted into optical signals with mutually different wavelengths and the wavelengths are multiplexed. Thus the two lines of image data are transmitted with one optical fiber. However, the scheme needs lenses, prisms, or the like for multiplexing, and has a problem in terms of reducing the size.

Figure 9B:
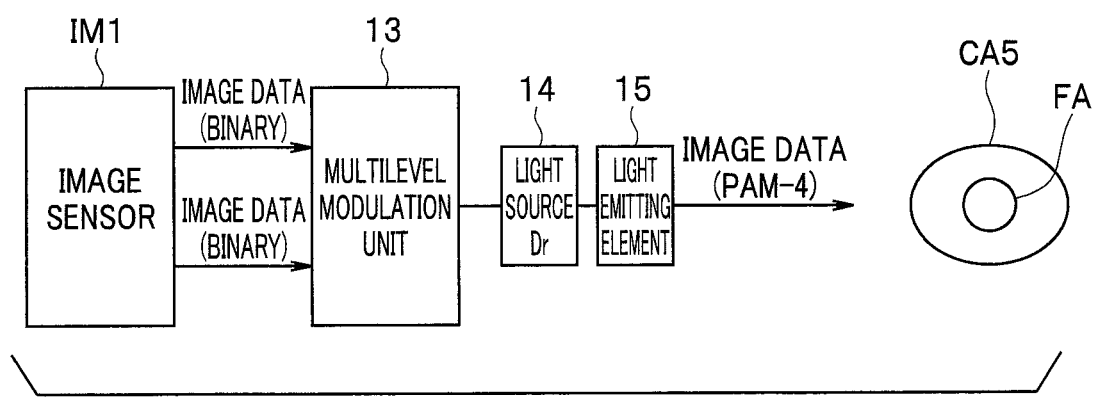
FIG. 9B is an explanatory diagram for explaining an advantage of the embodiment.

In contrast, in the above first embodiment, the microcontroller 31 sets the multilevel number N to 4 based on the scope information when outputting two lines of binary image data. That is, in the case, as shown in FIG. 9B, transmission with one optical fiber FA is possible at the same baud rate as in FIG. 9A. That is, since the multilevel modulation unit 13 can transmit 2-bit image data with one symbol in the configuration in FIG. 9B, a cable CA5 in which one optical fiber FA is wired should be adopted as a cable connecting the endoscope and the processor in optical transmission using a differential signal as well.

Figure 10B:
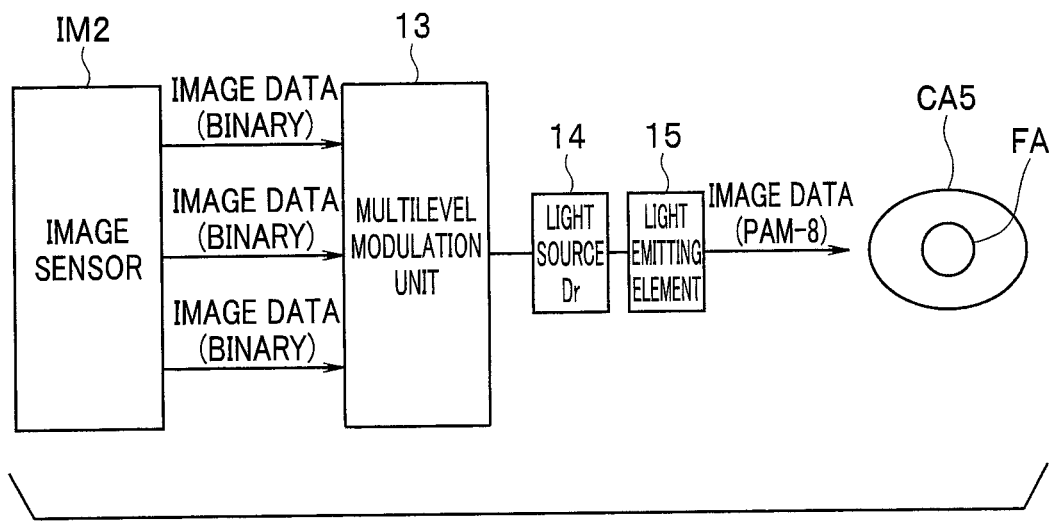
FIG. 10B is an explanatory diagram for explaining an advantage of the embodiment.

When three lines of binary image data are outputted as in FIG. 10A, the microcontroller 31 sets the multilevel number N to 8 based on the scope information. That is, in the case, as shown in FIG. 10B, threefold image data can be transmitted at the same baud rate as in FIG. 10A, and transmission using the cable CA5 in which one signal line FA is wired is possible.

As seen above, in the embodiment, by changing the multilevel number according to the number of pixels or the number of output lines, it is possible not only to commonize the number of signal lines in a cable but also to reduce the diameter.

Second Embodiment

Figure 11:
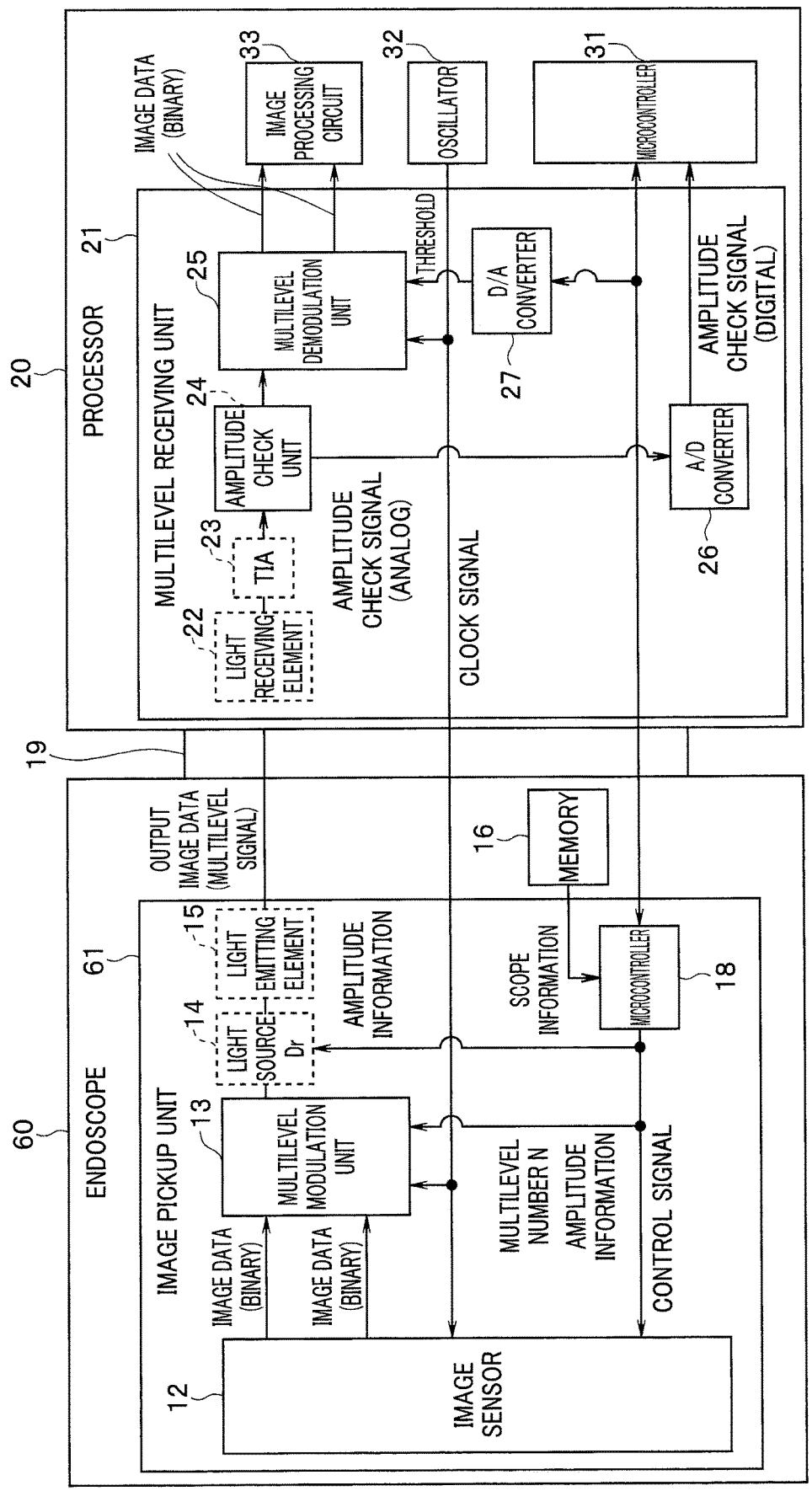
FIG. 11 is a block diagram showing a second embodiment of the present invention.

FIG. 11 is a block diagram showing a second embodiment of the present invention. In FIG. 11, the same component as in FIG. 1 is given the same sign, and the description is omitted. In the first embodiment, an example is described in which the scope information held by the endoscope is transferred to the microcontroller on the processor side, and the multilevel number is determined in the microcontroller. In contrast, in the embodiment, a microcontroller is provided in the endoscope, and the endoscope itself determines the multilevel number based on the scope information to perform multilevel modulation.

In FIG. 11, an endoscope 60 is different from the endoscope 10 in FIG. 1 in terms of adopting an image pickup unit 61 to which a microcontroller 18 is attached. The microcontroller 18 may read the scope information from the memory 16. The microcontroller 18 is configured to operate according to a program stored in a memory, not shown, to determine the multilevel number N in multilevel modulation based on the scope information similarly to the microcontroller 31. An approach of determining the multilevel number N of the microcontroller 18 is the same as the microcontroller 31, and the multilevel number is determined so that the multilevel number is decreased as much as possible while suppressing an increase in a signal frequency in transmission, for example, so that the multilevel number N is increased as the number of pixels of the image sensor 12 is larger, and the multilevel number N is decreased as the number of pixels of the image sensor 12 is smaller. For example, the microcontroller 18 may include a memory, not shown, configured to store a multilevel number table indicating a correspondence between the scope information and the multilevel number N, and refer to the multilevel number table stored in the memory based on the scope information to determine the multilevel number N.

When given information on the number of read pixels of the image sensor 12 or information on a frame rate from the microcontroller 31, the microcontroller 18 may also determine the multilevel number N taking the information into account.

In the embodiment, the microcontroller 18 is configured to give information on the multilevel number N not only to the multilevel modulation unit 13, but also to the microcontroller 31 through a signal line in the cable 19. The microcontroller 18 is also configured to receive the amplitude information generated by the microcontroller 31 for output to the multilevel modulation unit 13 and the light source driver 14.

Note that although described as being given the amplitude information from the microcontroller 31, the microcontroller 18 may be configured to receive amplitude check information based on an output of the amplitude check unit 24 in the processor 20, and acquire the amplitude information using the same approach as in the microcontroller 31.

The thus-configured embodiment is different from the first embodiment in that the multilevel number N is set by the microcontroller 18 in the endoscope 60. Accordingly, even when the processor 20 side does not have a function to determine the multilevel number, the endoscope 60 can change the multilevel number N in the multilevel modulation unit 13 based on the scope information.

Although the microcontroller 31 is described as receiving information on the multilevel number N from the microcontroller 18, it is not necessary to receive information on the multilevel number N from the microcontroller 18 when it is possible to identify the multilevel number N by checking an eye pattern of the received multilevel signal.

Other actions are the same as the first embodiment.

As seen above, the embodiment has the same effects as the first embodiment, and even when a function to determine the multilevel number is not provided on the processor side, it is possible to determine the multilevel number based on the scope information independently in the endoscope, and to enable always optimum and stable signal transmission irrespective of the configuration or the like of the endoscope, and the diameter can be reduced.

Modification

FIG. 12 is a block diagram showing a modification. The modification is such that the multilevel modulation unit 13 in the image pickup unit 11 in FIG. 1 is omitted, and an image sensor 71 incorporating a multilevel modulation unit 72 is adopted instead of the image sensor 12. In the multilevel modulation unit 72 in FIG. 12, the same component as in the multilevel modulation unit 13 in FIG. 2 is given the same sign, and the description is omitted.

The multilevel modulation unit 72 is different from the multilevel modulation unit 13 in FIG. 2 in that the multiplication circuit 46 and the clock buffer 47 are omitted. The multiplication circuit 46 and the clock buffer 47 are provided in the image sensor 71, and an output of the multiplication circuit 46 is supplied to the latch circuit 43 as an internal clock. Two lines of binary image data from a sensor unit 12a in the image sensor 71 are supplied to the data buffer 41a, 41b in the multilevel modulation unit 72.

Other components and actions are the same as in the embodiment in FIG. 1, and a difference is that an output of the image sensor 71 is multilevel image data.

The present invention is not limited to the above respective embodiments as they are, and can be embodied by modifying components within a scope not deviating from the gist at an implementation stage. In addition, a plurality of components disclosed in the above respective embodiments can be appropriately combined to form various inventions. For example, some components of all the components shown in the embodiments may be removed. Furthermore, components over different embodiments may be appropriately combined.

What is claimed is:

1. An endoscope system comprising:
a processor configured to be selectively connected to one of:
a first endoscope including:
a first image sensor comprising first pixels configured to pick up a first image and to output a first binary image signal;
a first multilevel modulation circuit configured to perform multilevel modulation on the first binary image signal and to output, through a predetermined transmission path, a first multilevel signal; and
a first memory configured to store first endoscope information including information on a first number of the first pixels of the first image sensor; on signal transmission; and
a second endoscope including:
a second image sensor comprising second pixels configured to pick up a second image and to output a second binary image signal;
a second multilevel modulation circuit configured to perform multilevel modulation on the second binary image signal and to output, through the predetermined transmission path, a second multilevel signal, and
a second memory configured to store second endoscope information including information on a second number of the second pixels of the second image sensor, wherein the second number of the second pixels is larger than the first number of the first pixels,
wherein the processor is configured to:
in response to the processor being connected to the first endoscope:
receive the first multilevel signal through the predetermined transmission path;
perform multilevel demodulation on the first multilevel signal received to generate the first binary image signal;
in response to the processor being connected to the second endoscope:
receive the second multilevel signal through the predetermined transmission path; and
perform multilevel demodulation on the second multilevel signal received to generate the second binary image signal;
in response to the processor being connected to the first endoscope:
read the first endoscope information from the first memory; and
set a first multilevel number in the multilevel modulation by the first multilevel modulation circuit based on the information on the first number of the first pixels of the first image sensor in the first endoscope information read; and
in response to the processor being connected to the second endoscope:
read the second endoscope information from the second memory; and
set a second multilevel number in the multilevel modulation by the second multilevel modulation circuit based on the information on the second number of the second pixels of the second image sensor in the second endo scope information read,
wherein the processor is configured to set the second multilevel number to be larger than the first multilevel number based on the second number of the second pixels being larger than the first number of the first pixels.

2. The endoscope system according to claim 1,
wherein the first endoscope information further includes at least one of information of a cable length, information of a cable diameter, and information of aged deterioration of a first cable that forms the predetermined transmission path between the first endoscope and the processor,
wherein the second endoscope information further includes at least one of information of a cable length, information of a cable diameter, and information of aged deterioration of a second cable that forms the predetermined transmission path between the second endoscope and the processor, and
wherein the processor is configured to:
set the first multilevel number based on the information on the first number of the first pixels of the first image sensor, a transmission rate of a signal transmitted through the predetermined transmission path and a margin between each value of the first multilevel signal and a threshold used for judgment of each value; and
set the second multilevel number based on the information on the second number of the second pixels of the first image sensor, a transmission rate of a signal transmitted through the predetermined transmission path and a margin between each value of the second multilevel signal and a threshold for judgment of each value.

3. The endoscope system according to claim 2,
wherein the processor is configured to:
set the first multilevel number based on the information on the first number of the first pixels of the first image sensor and at least one of the information of the cable length, the information of the cable diameter, the information of aged deterioration of the first cable, and information on a frame rate of output of the first image sensor; and
set the second multilevel number based on the information on the second number of the second pixels of the second image sensor and at least one of the information of the cable length, the information of the cable diameter, the information of aged deterioration of the second cable, and information of a frame rate of output of the second image sensor.

4. The endoscope system according to claim 1,
wherein the first endoscope information further includes at least one of information of a cable length, information of a cable diameter, and information of aged deterioration of a first cable that forms the predetermined transmission path between the first endoscope and the processor,
wherein the second endoscope information further includes at least one of information of a cable length, information of a cable diameter, and information of aged deterioration of a second cable that forms the predetermined transmission path between the second endoscope and the processor, and
wherein the processor is configured to:
set the first multilevel number using a same number of transmission paths irrespective of a number of output lines of the first binary image signal from the first image sensor; and
set the second multilevel number using a same number of transmission paths irrespective of a number of output lines of the second binary image signal from the second image sensor.

5. The endoscope system according to claim 4,
wherein the processor is configured to:
set the first multilevel number based on the information on the first number of the first pixels of the first image sensor and at least one of the information of the cable length, the information of the cable diameter, the information of aged deterioration of the first cable, and information on a frame rate of output of the first image sensor; and
set the second multilevel number based on the information on the second number of the second pixels of the second image sensor and at least one of the information of the cable length, the information of the cable diameter, the information of aged deterioration of the second cable, and information on a frame rate of out of the second image sensor.

6. The endoscope system according to claim 1, further comprising the first endoscope,
wherein the first multilevel modulation circuit is configured to output a single end signal or a differential signal.

7. The endoscope system according to claim 1, further comprising the first endoscope,
wherein the processor is configured to:
check an amplitude of the first multilevel signal received through the predetermined transmission path, and output an amplitude check signal; and
set a threshold used for judgment of each value of the first multilevel signal based on the amplitude check signal.

8. The endoscope system according to claim 7,
wherein the first multilevel modulation circuit is configured to change an amplitude of each value of the first multilevel signal based on the amplitude check signal.

* * * * *